(12) United States Patent
Rege et al.

(10) Patent No.: US 10,966,910 B2
(45) Date of Patent: Apr. 6, 2021

(54) ORAL CARE COMPOSITIONS AND METHODS OF USE

(71) Applicant: Colgate-Palmolive Company, New York, NY (US)

(72) Inventors: Aarti Rege, East Windsor, NJ (US); Michael Prencipe, West Windsor, NJ (US); Paul Thomson, Piscataway, NJ (US); Rehana Begum-Gafur, Clifton, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 16/841,735

(22) Filed: Apr. 7, 2020

(65) Prior Publication Data

US 2020/0253844 A1 Aug. 13, 2020

Related U.S. Application Data

(63) Continuation of application No. 15/848,009, filed on Dec. 20, 2017, now Pat. No. 10,646,420.

(60) Provisional application No. 62/437,091, filed on Dec. 21, 2016.

(51) Int. Cl.
| | | |
|---|---|---|
| *A61K 8/24* | (2006.01) |
| *A61Q 11/00* | (2006.01) |
| *A61K 8/21* | (2006.01) |
| *A61K 8/27* | (2006.01) |
| *A61K 8/20* | (2006.01) |

(52) U.S. Cl.
CPC ............... *A61K 8/24* (2013.01); *A61K 8/20* (2013.01); *A61K 8/21* (2013.01); *A61K 8/27* (2013.01); *A61Q 11/00* (2013.01)

(58) Field of Classification Search
CPC . A61Q 11/00; A61K 8/27; A61K 8/24; A61K 8/21; A61K 8/365; A61K 8/19; A61K 8/36; A61K 8/632
See application file for complete search history.

(56) References Cited

U.S. PATENT DOCUMENTS

| | | |
|---|---|---|
| 2,876,166 A | 3/1959 | Nebergall |
| 2,946,725 A | 7/1960 | Norris |
| 3,746,555 A | 7/1973 | Muhler |
| 4,961,924 A | 10/1990 | Suhonen |
| 5,004,597 A | 4/1991 | Majeti et al. |
| 5,188,820 A | 2/1993 | Cummins et al. |
| 5,578,293 A | 11/1996 | Prencipe et al. |
| 5,833,952 A | 11/1998 | Grigor et al. |
| 6,221,340 B1 | 4/2001 | Yu et al. |
| 6,685,920 B2 | 2/2004 | Baig et al. |
| 6,696,045 B2 | 2/2004 | Yue et al. |
| 8,906,347 B2 | 12/2014 | Strand et al. |
| 8,962,057 B2 | 2/2015 | Haught et al. |
| 9,962,322 B2 | 5/2018 | Vemishetti et al. |
| 9,968,803 B2 | 5/2018 | Fruge et al. |
| 10,098,822 B2 | 10/2018 | Rege et al. |
| 10,154,948 B2 | 12/2018 | Vemishetti et al. |
| 10,172,770 B2 | 1/2019 | Rege |
| 10,179,098 B2 | 1/2019 | Rege et al. |
| 10,258,551 B2 | 4/2019 | Rege et al. |
| 10,278,906 B2 | 5/2019 | Rege et al. |
| 2013/0209375 A1 | 8/2013 | Moya Argilagos et al. |
| 2015/0305993 A1 | 10/2015 | Rege et al. |
| 2016/0166498 A1 | 6/2016 | Anastassov et al. |
| 2016/0303010 A1 | 10/2016 | Prencipe et al. |
| 2017/0281476 A1 | 10/2017 | Midha et al. |
| 2017/0348206 A1 | 12/2017 | Vemishetti et al. |
| 2017/0367949 A1 | 12/2017 | Rege et al. |
| 2018/0168956 A1 | 6/2018 | Rege et al. |

FOREIGN PATENT DOCUMENTS

WO 2015/195139 12/2015

OTHER PUBLICATIONS

International Search Report and Written Opinion of the International Searching Authority in International Application No. PCT/US2017/067472, dated Feb. 27, 2018.

*Primary Examiner* — Nannette Holloman

(57) ABSTRACT

This invention relates to oral care compositions comprising zinc phosphate, a first source of stannous (e.g., stannous fluoride); and a second source of stannous, wherein the second source of stannous comprises stannous pyrophosphate, as well as to methods of using and of making these compositions.

13 Claims, No Drawings

ORAL CARE COMPOSITIONS AND METHODS OF USE

CROSS-REFERENCE TO RELATED PATENT APPLICATIONS

This application is a continuation of U.S. patent application Ser. No. 15/848,009, filed Dec. 20, 2017, which claims priority from U.S. Prov. Appl. No. 62/437,091, filed on Dec. 21, 2016, the contents of which are incorporated herein by reference in their entirety.

FIELD

This invention relates to oral care compositions comprising zinc phosphate a first stannous ion source, and a second stannous ion source, wherein the second stannous ion comprises stannous pyrophosphate, as well as to methods of using and making these compositions.

BACKGROUND

Oral care compositions present particular challenges in preventing microbial contamination.

Zinc is a known antimicrobial agent used in toothpaste compositions. Zinc is a known essential mineral for human health, and has been reported to help strengthen dental enamel and to promote cell repair. Unfortunately, conventional toothpaste formulations often require high concentrations of zinc, e.g., 2% by weight or more, to achieve efficacy. At this concentration, the zinc imparts a notably astringent taste to the composition. There is thus a need for improved antibacterial toothpaste formulations that do not suffer from the drawbacks of conventional compositions.

Stannous ions, in particular stannous salts such as stannous fluoride, are also known anti-microbial agents and are used in various dentifrices as agents for preventing plaque. However, there are certain disadvantages to using stannous salts, such as instability, tendency to stain teeth, astringency, and unpleasant taste for users.

Zinc phosphate $(Zn_3(PO_4)_2)$ is insoluble in water, although soluble in acidic or basic solutions, e.g., solutions of mineral acids, acetic acid, ammonia, or alkali hydroxides. See, e.g., Merck Index, $13^{th}$ Ed. (2001) p. 1812, monograph number 10205. Partly because it is viewed in the art as a generally inert material, zinc phosphate is commonly used in dental cements, for example in cementation of inlays, crowns, bridges, and orthodontic appliances, which are intended to endure in the mouth for many years. Zinc phosphate dental cements are generally prepared by mixing zinc oxide and magnesium oxide powders with a liquid consisting principally of phosphoric acid, water, and buffers, so the cement comprising zinc phosphate is formed in situ by reaction with phosphoric acid.

Oral care compositions which contain stannous ion sources exhibit excellent clinical benefits, particularly in the reduction of gingivitis and in the treatment or prevention of erosive tooth demineralization. Stannous fluoride is well known for use in clinical dentistry with a history of therapeutic benefits over forty years. However, until recently, its popularity has been limited by its instability in aqueous solutions. The instability of stannous fluoride in water is primarily due to the reactivity of the stannous ion $(Sn^{2+})$. Stannous salts readily hydrolyse above a pH of 4, resulting in precipitation from solution, with a consequent loss of the therapeutic properties.

One way to overcome the stability problems with stannous ions is to limit the amount of water in the composition to very low levels, or to use a dual phase system. Both of these solutions to the stannous ion problem have drawbacks. Low water oral care compositions can be difficult to formulate with desired rheological properties, and dual-phase compositions are considerably more expensive to manufacture and package.

Accordingly, in view of the drawbacks and disadvantages to using various antimicrobials, such as zinc and stannous, there is a need for oral care compositions with anti-bacterial efficacy, but which are also palatable and desirable for a user.

BRIEF SUMMARY

The inclusion of a zinc source comprising zinc phosphate, selected at certain concentrations and amounts, increases or improves the delivery of stannous in the oral cavity of a user. The delivery or availability of Sn is improved in the current invention, where the improvement is relative to comparable products currently on the market.

In one aspect the invention is an oral care composition (Composition 1.0) comprising:
A zinc source comprising zinc phosphate;
a first source of stannous (e.g., stannous fluoride); and
a second source of stannous, wherein the second source of stannous comprises stannous pyrophosphate.

For example, the invention contemplates any of the following compositions (unless otherwise indicated, values are given as percentage of the overall weight of the composition)

1.1 Composition 1, wherein the zinc phosphate is a preformed salt of zinc phosphate (e.g., zinc phosphate hydrate).

1.2 Any preceding composition, wherein the amount of zinc phosphate is from 0.05 to 10% by weight, relative to the weight of the oral care composition, for example, from 0.1 to 8% by weight, or from 0.5 to 5% by weight, or from 0.5 to 4% by weight, or from 1 to 4%, or from 1 to 3% by weight, or from 2 to 3% by weight, or about 1% or about 2%, or about 2.25% or about 2.5%, by weight.

1.3 Any of the preceding compositions, wherein the amount of stannous pyrophosphate is from 0.1%-3% by wt. of the composition. (e.g., about 1% by wt. of the composition).

1.4 Any of the preceeding compositions wherein the amount of stannous pyrophosphate is about 0.2% by wt.

1.5 Any of the compositions 1.1-1.4 wherein the amount of stannous pyrophosphate is about 0.3% by wt.

1.6 Any of the compositions 1.1-1.4 wherein the amount of stannous pyrophosphate is about 0.5% by wt.

1.7 Any of the compositions 1.1-1.4 wherein the amount of stannous pyrophosphate is about 0.75% by wt.

1.8 Any of the compositions 1.1-1.4 wherein the amount of stannous pyrophosphate is about 1.0% by wt.

1.9 Any of the preceding composition, wherein the first stannous ion source is stannous fluoride, other stannous halides such as stannous chloride dihydrate, stannous pyrophosphate, organic stannous carboxylate salts such as stannous formate, acetate, gluconate, lactate, tartrate, oxalate, malonate and citrate, stannous ethylene glyoxide, or a mixture thereof.

1.10 Composition of 1.14, wherein the first stannous ion source is stannous fluoride (e.g., about 0.45 wt %; e.g., about 0.454 wt %.)

1.11 Any of the preceding compositions further comprising a fluoride source selected from: stannous fluoride, sodium fluoride, potassium fluoride, sodium monofluorophosphate, sodium fluorosilicate, ammonium fluorosilicate, amine fluoride (e.g., N'-octadecyltrimethylendiamine-N,N,N'-tris(2-ethanol)-dihydrofluoride), ammonium fluoride, titanium fluoride, hexafluorosulfate, and combinations thereof 1.12 Any of the preceding compositions wherein the pH is between 7.5 and 10.5.

1.13 Any of the preceding compositions further comprising an effective amount of one or more alkali phosphate salts, e.g., sodium, potassium or calcium salts, e.g., selected from alkali dibasic phosphate and alkali pyrophosphate salts, e.g., alkali phosphate salts selected from sodium phosphate dibasic, potassium phosphate dibasic, dicalcium phosphate dihydrate, calcium pyrophosphate, tetrasodium pyrophosphate, tetrapotassium pyrophosphate, sodium tripolyphosphate, disodium hydrogen orthophosphate, monosodium phosphate, pentapotassium triphosphate and mixtures of any of two or more of these, e.g., in an amount of 1-20%, e.g., 2-8%, e.g., ca. 5%>, by weight of the composition.

1.14 The alkali phosphate salt of 1.13, wherein the salt comprises tetrapotassium pyrophosphate 1.15 The composition of 1.14, wherein the tetrasodium pyrophosphate is from 0.1-3.0 wt % (e.g., about 2.0 wt %).

1.16 The composition of 1.13, wherein the salt comprises sodium tripolyphosphate.

1.17 The composition of 1.16, wherein sodium tripolyphosphate is from 0.1-3.0 wt % (e.g., about 2.0 wt %).

1.18 Any of the preceding compositions further comprising an abrasive or particulate (e.g., silica).

1.19 Any of the preceding compositions wherein the silica is synthetic amorphous silica. (e.g., 1%-28% by wt.) (e.g., 8%-25% by wt.)

1.20 Any of the preceding composition wherein the silica abrasives are silica gels or precipitated amorphous silicas, e.g. silicas having an average particle size ranging from 2.5 microns to 12 microns.

1.21 Any of the preceding compositions further comprising a small particle silica having a median particle size (d50) of 1-5 microns (e.g., 3-4 microns) (e.g., about 5 wt. % Sorbosil AC43 from PQ Corporation, Warrington, United Kingdom).

1.22 Any of the preceding compositions wherein 20-30 wt % of the total silica in the composition is small particle silica (e.g., having a median particle size (d50) of 3-4 microns) and wherein the small particle silica is about 5 wt. % of the oral care composition.

1.23 Any of the preceding compositions comprising silica wherein the silica is used as a thickening agent, e.g., particle silica.

1.24 Any of the preceding compositions further comprising glycerin, wherein the glycerin is in a total amount of 2.0-5.0% (e.g., about 4%)

1.25 The composition of 1.24, wherein the glycerin is in an amount of about 4% by wt. of the composition.

1.26 Any of the preceding compositions, wherein the composition comprises an aqueous buffer system, for example, wherein the buffer system comprises an organic acid and an alkali metal salt thereof, e.g., wherein the organic acid is citric acid and the salt is a mono-, di- and/or tri-alkali metal citrate salt, e.g., mono-, di- and/or tri-lithium, sodium, potassium, or cesium citrate salt, and citric acid.)

1.27 Composition of 1.26, wherein the buffer system comprises trisodium citrate and citric acid (e.g., 1 to 10% by weight of the composition) (e.g., 1.2% by wt. of the composition). For example, the molar ratio of mono-, di- and/or tri-sodium citrate and citric acid is 1.5 to 5, (e.g., 2 to 4).

1.28 Composition of 1.26 or 1.27, wherein the buffer is a citrate buffer comprising sodium citrate (e.g., about 1.0% wt.) and citric acid (e.g., about 0.2% wt.)

1.29 Any of the preceding compositions comprising polymer films.

1.30 Any of the preceding compositions comprising flavoring, fragrance and/or coloring.

1.31 Any of the preceding compositions, wherein the composition comprises a thickening agents selected from the group consisting of carboxyvinyl polymers, carrageenan, hydroxyethyl cellulose and water soluble salts of cellulose ethers (e.g., sodium carboxymethyl cellulose and sodium carboxymethyl hydroxyethyl cellulose).

1.32 Any of the preceding compositions, wherein the compositions comprises sodium carboxymethyl cellulose (e.g., from 0.5 wt. %-1.5 wt. %)

1.33 Any of the preceding compositions comprising from 5%-40%, e.g., 10%-35%, e.g., about 10%, 15%, 25%, 30%, and 35% water.

1.34 Any of the preceding compositions comprising an additional antibacterial agent selected from halogenated diphenyl ether (e.g. triclosan), herbal extracts and essential oils (e.g., rosemary extract, tea extract, magnolia extract, thymol, menthol, eucalyptol, geraniol, carvacrol, citral, hinokitol, catechol, methyl salicylate, epigallocatechin gallate, epigallocatechin, gallic acid, miswak extract, sea-buckthorn extract), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, metal ions (e.g., zinc salts, for example, Zinc Chloride, Zinc Lactate, Zinc Sulfate, stannous salts, copper salts, iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol and other piperidino derivatives, nicin preparations, chlorite salts; and mixtures of any of the foregoing.

1.35 Any of the preceding compositions comprising an antioxidant, e.g., selected from the group consisting of Co-enzyme Q10, PQQ, Vitamin C, Vitamin E, Vitamin A, BHT, anethole-dithiothione, and mixtures thereof.

1.36 Any of the preceding compositions comprising a whitening agent.

1.37 Any of the preceding compositions comprising a whitening agent selected from a whitening active selected from the group consisting of peroxides, metal chlorites, perborates, percarbonates, peroxyacids, hypochlorites, and combinations thereof.

1.38 The composition of 1.36, wherein the whitening agent is titanium dioxide.

1.39 Any of the preceding compositions further comprising hydrogen peroxide or a hydrogen peroxide source, e.g., urea peroxide or a peroxide salt or complex (e.g., such as peroxyphosphate, peroxycarbonate, perborate, peroxysilicate, or persulphate salts; for example calcium peroxyphosphate, sodium perborate, sodium carbonate peroxide, sodium peroxyphosphate, and potassium persulfate), or hydrogen peroxide polymer complexes such as hydrogen peroxide-polyvinyl pyrrolidone polymer complexes.

1.40 Any of the preceding compositions further comprising an anionic surfactant, e.g., (e.g., sodium lauryl sulfate).

1.41 Any of the preceding compositions further comprising microcrystalline cellulose and/or sodium carboxymethylcellulose, e.g., in an amount of from 0.1-5%, e.g., 0.5-2%, e.g. 1%.

1.42 Any of the preceding compositions further comprising polyethylene glycol in an amount of from 1-6% (e.g., 2% wt.).

1.43 Any of the preceding compositions further comprising an agent that interferes with or prevents bacterial attachment, e.g., ELA or chitosan.

1.44 Any of the preceding compositions comprising:
Zinc phosphate about 1.0 wt %
Stannous pyrophosphate about 0.2 wt %
Tetrasodium pyrophosphate about 2.0 wt %

1.45 Any of the preceding compositions comprising:
Zinc phosphate about 1.0 wt %
Stannous pyrophosphate about 0.3 wt %
Tetrasodium pyrophosphate about 2.0 wt %

1.46 Any of 1.0-1.43, wherein the composition comprises
Zinc phosphate about 1.7 wt %
Stannous pyrophosphate about 1.0 wt %
Tetrasodium pyrophosphate about 2.0 wt %

1.47 Any of Composition 1.44-1.46 further comprising a citrate buffer system, wherein the buffer system comprises tri-sodium citrate and citric acid (e.g., the buffer system being about 1.2 wt % of the composition).

1.48 Any of the preceding compositions effective upon application to the oral cavity, e.g., by rinsing, optionally in conjunction with brushing, to (i) reduce or inhibit formation of dental caries, (ii) reduce, repair or inhibit pre-carious lesions of the enamel, e.g., as detected by quantitative light-induced fluorescence (QLF) or electrical caries measurement (ECM), (iii) reduce or inhibit demineralization and promote remineralization of the teeth, (iv) reduce hypersensitivity of the teeth, (v) reduce or inhibit gingivitis, (vi) promote healing of sores or cuts in the mouth, (vii) reduce levels of acid producing bacteria, (viii) to increase relative levels of arginolytic bacteria, (ix) inhibit microbial biofilm formation in the oral cavity, (x) raise and/or maintain plaque pH at levels of at least pH 5.5 following sugar challenge, (xi) reduce plaque accumulation, (xii) treat, relieve or reduce dry mouth, (xiii) clean the teeth and oral cavity (xiv) reduce erosion, (xv) prevents stains and/or whiten teeth, (xvi) immunize the teeth against cariogenic bacteria; and/or (xvii) promote systemic health, including cardiovascular health, e.g., by reducing potential for systemic infection via the oral tissues.

1.49 Any of the preceding oral compositions, wherein the oral composition may be any of the following oral compositions selected from the group consisting of: a toothpaste or a dentifrice, a mouthwash or a mouth rinse, a topical oral gel, and a denture cleanser.

1.50 A composition obtained or obtainable by combining the ingredients as set forth in any of the preceding compositions.

1.51 Any preceding compositions, wherein zinc phosphate is the only source of zinc.

1.52 Any of the preceding compositions, wherein stannous fluoride and stannous pyrophosphate are the only sources of stannous.

1.53 Any of the preceding compositions, wherein the humectant is selected from the group consisting of: edible polyhydric alcohols (e.g., glycerin, sorbitol, xylitol, propylene glycol), polyols and mixtures thereof.

1.54 Any of the preceding compositions, wherein the humectant is sorbitol (e.g., about 40 wt. %, about 41%, or about 42 wt. %)

1.55 A composition obtained or obtainable by combining the ingredients as set forth in any of the preceding compositions.

1.56 A composition for use as set for in any of the preceding compositions.

In another embodiment, the invention encompasses a method to improve oral health comprising applying an effective amount of the oral composition of any of the embodiments set forth above to the oral cavity of a subject in need thereof, e.g., a method to i. reduce or inhibit formation of dental caries,
ii. reduce, repair or inhibit early enamel lesions, e.g., as detected by quantitative light-induced fluorescence (QLF) or electrical caries measurement(ECM),
iii. reduce or inhibit demineralization and promote remineralization of the teeth,
iv. reduce hypersensitivity of the teeth,
v. reduce or inhibit gingivitis,
vi. promote healing of sores or cuts in the mouth,
vii. reduce levels of acid producing bacteria,
viii. to increase relative levels of arginolytic bacteria,
ix. inhibit microbial bio film formation in the oral cavity,
x. raise and/or maintain plaque pH at levels of at least pH 5.5 following sugar challenge,
xi. reduce plaque accumulation,
xii. treat dry mouth,
xiii. enhance systemic health, including cardiovascular health, e.g., by reducing potential for systemic infection via the oral tissues,
xiv. Whiten teeth,
xv. reduce erosion of the teeth,
xvi. immunize (or protect) the teeth against cariogenic bacteria and their effects, and/or
xvii. clean the teeth and oral cavity.

The invention further comprises the use of sodium bicarbonate, sodium methyl cocoyl taurate (tauranol), MIT, and benzyl alcohol and combinations thereof in the manufacture of a Composition of the Invention, e.g., for use in any of the indications set forth in the above method of Composition 1.0, et seq.

DETAILED DESCRIPTION

As used herein, the term "oral composition" means the total composition that is delivered to the oral surfaces. The composition is further defined as a product which, during the normal course of usage, is not, the purposes of systemic administration of particular therapeutic agents, intentionally swallowed but is rather retained in the oral cavity for a time sufficient to contact substantially all of the dental surfaces and/or oral tissues for the purposes of oral activity. Examples of such compositions include, but are not limited to, toothpaste or a dentifrice, a mouthwash or a mouth rinse, a topical oral gel, a denture cleanser, and the like.

As used herein, the term "dentifrice" means paste, gel, or liquid formulations unless otherwise specified. The dentifrice composition can be in any desired form such as deep striped, surface striped, multi-layered, having the gel surrounding the paste, or any combination thereof. Alternatively the oral composition may be dual phase dispensed from a separated compartment dispenser.

Stannous Ion Source

In some embodiments, the first stannous source comprises a stannous source selected from stannous fluoride, other stannous halides such as stannous chloride dihydrate, stannous pyrophosphate, organic stannous carboxylate salts such as stannous formate, acetate, gluconate, lactate, tartrate, oxalate, malonate and citrate, stannous ethylene glyoxide, or mixtures thereof. In some embodiments, the first stannous source comprises stannous fluoride.

Fluoride Ion Source

The oral care compositions may further include one or more fluoride ion sources, e.g., soluble fluoride salts. A wide variety of fluoride ion-yielding materials can be employed as sources of soluble fluoride in the present compositions. Examples of suitable fluoride ion-yielding materials are found in U.S. Pat. No. 3,535,421, to Briner et al.; U.S. Pat. No. 4,885,155, to Parran, Jr. et al. and U.S. Pat. No. 3,678,154, to Widder et al., each of which are incorporated herein by reference. Representative fluoride ion sources used with the present invention (e.g., Composition 1.0 et seq.) include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source includes stannous fluoride, sodium fluoride, sodium monofluorophosphate as well as mixtures thereof. Where the formulation comprises calcium salts, the fluoride salts are preferably salts wherein the fluoride is covalently bound to another atom, e.g., as in sodium monofluorophosphate, rather than merely ionically bound, e.g., as in sodium fluoride.

Surfactants

The invention may in some embodiments contain anionic surfactants, e.g., the Compositions of Composition 1.0, et seq., for example, water-soluble salts of higher fatty acid monoglyceride monosulfates, such as the sodium salt of the monosulfated monoglyceride of hydrogenated coconut oil fatty acids such as sodium N-methyl N-cocoyl taurate, sodium cocomo-glyceride sulfate; higher alkyl sulfates, such as sodium lauryl sulfate; higher alkyl-ether sulfates, e.g., of formula $CH_3(CH_2)_mCH_2(OCH_2CH_2)_nOSO_3X$, wherein m is 6-16, e.g., 10, n is 1-6, e.g., 2, 3 or 4, and X is Na or, for example sodium laureth-2 sulfate $(CH_3(CH2)_{10}CH_2(OCH_2CH_2)_2OSO_3Na)$; higher alkyl aryl sulfonates such as sodium dodecyl benzene sulfonate (sodium lauryl benzene sulfonate); higher alkyl sulfoacetates, such as sodium lauryl sulfoacetate (dodecyl sodium sulfoacetate), higher fatty acid esters of 1,2 dihydroxy propane sulfonate, sulfocolaurate (N-2-ethyl laurate potassium sulfoacetamide) and sodium lauryl sarcosinate. By "higher alkyl" is meant, e.g., $C_{6-30}$ alkyl. In particular embodiments, the anionic surfactant (where present) is selected from sodium lauryl sulfate and sodium ether lauryl sulfate. When present, the anionic surfactant is present in an amount which is effective, e.g., >0.001% by weight of the formulation, but not at a concentration which would be irritating to the oral tissue, e.g., 1%, and optimal concentrations depend on the particular formulation and the particular surfactant. In one embodiment, the anionic surfactant is present at from 0.03% to 5% by weight, e.g., 1.5%.

In another embodiment, cationic surfactants useful in the present invention can be broadly defined as derivatives of aliphatic quaternary ammonium compounds having one long alkyl chain containing 8 to 18 carbon atoms such as lauryl trimethylammonium chloride, cetyl pyridinium chloride, cetyl trimethylammonium bromide, di-isobutylphenoxyethyldimethylbenzylammonium chloride, coconut alkyltrimethylammonium nitrite, cetyl pyridinium fluoride, and mixtures thereof. Illustrative cationic surfactants are the quaternary ammonium fluorides described in U.S. Pat. No. 3,535,421, to Briner et al., herein incorporated by reference. Certain cationic surfactants can also act as germicides in the compositions.

Illustrative nonionic surfactants of Composition 1.0, et seq., that can be used in the compositions of the invention can be broadly defined as compounds produced by the condensation of alkylene oxide groups (hydrophilic in nature) with an organic hydrophobic compound which may be aliphatic or alkylaromatic in nature. Examples of suitable nonionic surfactants include, but are not limited to, the Pluronics, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures of such materials.

Illustrative amphoteric surfactants of Composition 1.0, et seq., that can be used in the compositions of the invention include betaines (such as cocamidopropylbetaine), derivatives of aliphatic secondary and tertiary amines in which the aliphatic radical can be a straight or branched chain and wherein one of the aliphatic substituents contains about 8-18 carbon atoms and one contains an anionic water-solubilizing group (such as carboxylate, sulfonate, sulfate, phosphate or phosphonate), and mixtures of such materials.

The surfactant or mixtures of compatible surfactants can be present in the compositions of the present invention in 0.1% to 5%, in another embodiment 0.3% to 3% and in another embodiment 0.5% to 2% by weight of the total composition.

Flavoring Agents

The oral care compositions of the invention may also include a flavoring agent. Flavoring agents which are used in the practice of the present invention include, but are not limited to, essential oils and various flavoring aldehydes, esters, alcohols, and similar materials, as well as sweeteners such as sodium saccharin. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Certain embodiments employ the oils of peppermint and spearmint.

The flavoring agent is incorporated in the oral composition at a concentration of 0.01 to 1% by weight.

Chelating and Anti-Calculus Agents

The oral care compositions of the invention also may include one or more chelating agents able to complex calcium found in the cell walls of the bacteria. Binding of this calcium weakens the bacterial cell wall and augments bacterial lysis.

Another group of agents suitable for use as chelating or anti-calculus agents in the present invention are the soluble pyrophosphates. The pyrophosphate salts used in the present compositions can be any of the alkali metal pyrophosphate salts. In certain embodiments, salts include tetra alkali metal pyrophosphate, dialkali metal diacid pyrophosphate, trialkali metal monoacid pyrophosphate and mixtures thereof, wherein the alkali metals are sodium or potassium. The salts are useful in both their hydrated and unhydrated forms. An effective amount of pyrophosphate salt useful in the present composition is generally enough to provide at least 0.1 wt. % pyrophosphate ions, e.g., 0.1 to 3 wt 5, e.g., 0.1 to 2 wt %, e.g., 0.1 to 1 wt %, e.g., 0.2 to 0.5 wt %. The pyrophosphates also contribute to preservation of the compositions by lowering water activity.

In various embodiments of the present disclosure (e.g., Composition 1.0 et seq), the compositions further comprise one or more anticalculus (tartar control) agents. Suitable anticalculus agents include without limitation mono-phosphates (e.g. monobasic, dibasic or tribasic phosphate) and P1-6 polyphosphates (e.g., pyrophosphates, tripolyphosphate, tetraphosphates and hexametaphosphate salts, zinc salts (e.g., zinc citrate, zinc chloride, zinc citrate trihydrate), Gantrez® (a copolymer of methylvinyl ether (PVM) and maleic acid (MA)), polyaminopropanesulfonic acid (AMPS), polypeptides, polyolefin sulfonates, polyolefin phosphates, and diphosphonates. In certain embodiments, the other anticalculus agents are alkali and/or alkaline earth metal phosphate salts, for example, sodium, potassium or calcium salts. In certain embodiments, the composition includes mono-phosphates (e.g. monobasic, dibasic or tribasic phosphate), P1-6 polyphosphates, Gantrez, or a combination thereof. Still in certain embodiments, the composition includes sodium tripolyphosphate, tetrasodium pyrophosphate, Gantrez, or a combination thereof Polymers The oral care compositions of the invention also optionally include one or more polymers, such as polyethylene glycols, polyvinyl methyl ether maleic acid copolymers, polysaccharides (e.g., cellulose derivatives, for example carboxymethyl cellulose, or polysaccharide gums, for example xanthan gum or carrageenan gum). Acidic polymers, for example polyacrylate gels, may be provided in the form of their free acids or partially or fully neutralized water soluble alkali metal (e.g., potassium and sodium) or ammonium salts. Certain embodiments include 1:4 to 4:1 copolymers of maleic anhydride or acid with another polymerizable ethylenically unsaturated monomer, for example, methyl vinyl ether (methoxyethylene) having a molecular weight (M.W.) of about 30,000 to about 1,000,000. These copolymers are available for example as Gantrez AN 139 (M.W. 500,000), AN 1 19 (M.W. 250,000) and S-97 Pharmaceutical Grade (M.W. 70,000), of GAF Chemicals Corporation.

Other operative polymers include those such as the 1:1 copolymers of maleic anhydride with ethyl acrylate, hydroxyethyl methacrylate, N-vinyl-2-pyrollidone, or ethylene, the latter being available for example as Monsanto EMA No. 1 103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone.

Suitable generally, are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers contain sufficient carboxylic salt groups for water-solubility.

A further class of polymeric agents includes a composition containing homopolymers of substituted acrylamides and/or homopolymers of unsaturated sulfonic acids and salts thereof, in particular where polymers are based on unsaturated sulfonic acids selected from acrylamidoalykane sulfonic acids such as 2-acrylamide 2 methylpropane sulfonic acid having a molecular weight of about 1,000 to about 2,000,000, described in U.S. Pat. No. 4,842,847, Jun. 27, 1989 to Zahid, incorporated herein by reference.

In preparing oral care compositions, it is sometimes necessary to add some thickening material to provide a desirable consistency or to stabilize or enhance the performance of the formulation. In certain embodiments, the thickening agents are carboxyvinyl polymers, carrageenan, xanthan, hydroxyethyl cellulose and water soluble salts of cellulose ethers such as sodium carboxymethyl cellulose and sodium carboxymethyl hydroxyethyl cellulose. Natural gums such as karaya, gum arabic, and gum tragacanth can also be incorporated. Colloidal magnesium aluminum silicate or finely divided silica can be used as component of the thickening composition to further improve the composition's texture. In certain embodiments, thickening agents in an amount of about 0.5% to about 5.0% by weight of the total composition are used.

Abrasives

Natural calcium carbonate is found in rocks such as chalk, limestone, marble and travertine. It is also the principle component of egg shells and the shells of mollusks. The natural calcium carbonate abrasive of the invention is typically a finely ground limestone which may optionally be refined or partially refined to remove impurities. For use in the present invention, the material has an average particle size of less than 10 microns, e.g., 3-7 microns, e.g. about 5.5 microns. For example a small particle silica may have an average particle size (D50) of 2.5-4.5 microns. Because natural calcium carbonate may contain a high proportion of relatively large particles of not carefully controlled, which may unacceptably increase the abrasivity, preferably no more than 0.01%, preferably no more than 0.004% by weight of particles would not pass through a 325 mesh. The material has strong crystal structure, and is thus much harder and more abrasive than precipitated calcium carbonate. The tap density for the natural calcium carbonate is for example between 1 and 1.5 g/cc, e.g., about 1.2 for example about 1.19 g/cc. There are different polymorphs of natural calcium carbonate, e.g., calcite, aragonite and vaterite, calcite being preferred for purposes of this invention. An example of a commercially available product suitable for use in the present invention includes Vicron® 25-11 FG from GMZ.

Precipitated calcium carbonate is generally made by calcining limestone, to make calcium oxide (lime), which can then be converted back to calcium carbonate by reaction with carbon dioxide in water. Precipitated calcium carbonate has a different crystal structure from natural calcium carbonate. It is generally more friable and more porous, thus having lower abrasivity and higher water absorption. For use in the present invention, the particles are small, e.g., having an average particle size of 1-5 microns, and e.g., no more than 0.1%, preferably no more than 0.05% by weight of particles which would not pass through a 325 mesh. The particles may for example have a D50 of 3-6 microns, for example 3.8=4.9, e.g., about 4.3; a D50 of 1-4 microns, e.g. 2.2-2.6 microns, e.g., about 2.4 microns, and a D10 of 1-2 microns, e.g., 1.2-1.4, e.g. about 1.3 microns. The particles have relatively high water absorption, e.g., at least 25 g/100 g, e.g. 30-70 g/100 g. Examples of commercially available products suitable for use in the present invention include, for example, Carbolag® 15 Plus from Lagos Industria Quimica.

In certain embodiments the invention may comprise additional calcium-containing abrasives, for example calcium phosphate abrasive, e.g., tricalcium phosphate ($Ca_3(PO_4)_2$), hydroxyapatite ($Ca_{10}(PO_4)_6(OH)_2$), or dicalcium phosphate dihydrate ($CaHPO_4.2H_2O$, also sometimes referred to herein as DiCal) or calcium pyrophosphate, and/or silica abrasives, sodium metaphosphate, potassium metaphosphate, aluminum silicate, calcined alumina, bentonite or other siliceous materials, or combinations thereof. Any silica suitable for oral care compositions may be used, such as precipitated silicas or silica gels. For example synthetic amorphous silica. Silica may also be available as a thickening agent, e.g., particle silica. For example, the silica can also be small particle silica (e.g., Sorbosil AC43 from PQ Corporation, Warrington, United Kingdom). However the additional abrasives are preferably not present in a type or amount so as to increase the RDA of the dentifrice to levels which could damage sensitive teeth, e.g., greater than 130.

Water

Water is present in the oral compositions of the invention (e.g., Composition 1.0 et seq). Water, employed in the preparation of commercial oral compositions should be deionized and free of organic impurities. Water commonly makes up the balance of the compositions and includes 5% to 45%, e.g., 10% to 20%, e.g., 25-35%, by weight of the oral compositions. This amount of water includes the free water which is added plus that amount which is introduced with other materials such as with sorbitol or silica or any components of the invention. The Karl Fischer method is a one measure of calculating free water.

Humectants

Within certain embodiments of the oral compositions (e.g. Composition 1.0 et seq), it is also desirable to incorporate a humectant to reduce evaporation and also contribute towards preservation by lowering water activity. Certain humectants can also impart desirable sweetness or flavor to the compositions. The humectant, on a pure humectant basis, generally includes 15% to 70% in one embodiment or 30% to 65% in another embodiment by weight of the composition.

Suitable humectants include edible polyhydric alcohols such as glycerine, sorbitol, xylitol, propylene glycol as well as other polyols and mixtures of these humectants. Mixtures of glycerine and sorbitol may be used in certain embodiments as the humectant component of the compositions herein.

The present invention in its method aspect involves applying to the oral cavity a safe and effective amount of the compositions described herein.

The compositions and methods according to the invention (e.g., Composition 1.0 et seq) can be incorporated into oral compositions for the care of the mouth and teeth such as toothpastes, transparent pastes, gels, mouth rinses, sprays and chewing gum.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls. It is understood that when formulations are described, they may be described in terms of their ingredients, as is common in the art, notwithstanding that these ingredients may react with one another in the actual formulation as it is made, stored and used, and such products are intended to be covered by the formulations described.

The following examples further describe and demonstrate illustrative embodiments within the scope of the present invention. The examples are given solely for illustration and are not to be construed as limitations of this invention as many variations are possible without departing from the spirit and scope thereof. Various modifications of the invention in addition to those shown and described herein should be apparent to those skilled in the art and are intended to fall within the appended claims.

Example 1

TABLE 1

| Dentifrice Formulation A | |
|---|---|
| Ingredient | Weight % |
| DEMINERALIZED WATER | Q.S. (e.g., 15-35%) |
| CITRIC ACID - ANHYDROUS USP, EP | 0.20 |
| TRISODIUM CITRATE DIHYDRATE - USP | 1.0 |
| STANNOUS FLUORIDE, USP | 0.454 |
| Zinc Phosphate, hydrate | 0.5-2.0% |
| SORBITOL - NON-CRYSTAL - 70% SOLN USP, EP | 38.0-43.0% |
| POLYETHYLENE GLYCOL 600 | 2.0 |
| Thickeners | 1.5-2.0% |
| STANNOUS PYROPHOSPHATE | 0.2-1.5% |
| Abrasives | 20.0 |
| TETRASODIUM PYROPHOSPHATE - FINE FCC | 2.0 |
| Anionic Surfactant | 1.5 |
| Amphoteric Surfactant | 1.25 |
| Flavors, Colors and Sweeteners | 1.0-2.0 |
| 99%-101% Glycerin | 4.0 |
| Total Components | 100.0 |

Example 2

TABLE 2

Stannous Stability

| Description | Aging Time pt | Initial % Sol. Tin | Aged % Sol. Tin | Initial % Sol. Zn | Aged % Sol. Zinc | Initial % F | Aged % Sol. F |
|---|---|---|---|---|---|---|---|
| SnF + 1% ZnP, 0.2% SnPyro, 1.2% Buffer (Composition A) | Initial 25 C.<br>4 wks(40 C.)<br>8 wks(40 C.)<br>13 wks(40 C.) | 0.37 | 0.26<br>0.29<br>0.27 | 0.48 | 0.25<br>0.24<br>0.28 | 1117 | 1030<br>1042<br>981 |
| SnF + 1% ZnP, 0.3% SnPyro, 1.2% Buffer (Composition B) | Initial 25 C.<br>4 wks(40 C.)<br>8 wks<br>13 wks | 0.4 | 0.3<br>0.31<br>0.3 | 0.24 | 0.25<br>0.25<br>0.25 | 1116 | 1047<br>1026<br>956 |
| SnF + 1% ZnP, 0.5% SnPyro, 1.2% Buffer (Composition C) | Initial 25 C.<br>4 wks(40 C.)<br>8 wks (40 C.)<br>13 wks (25 C./40 C.) | 0.51 | 0.47<br>0.49<br>0.50/0.45 | 0.27 | 0.31<br>0.3<br>0.35/0.32 | 1105 | 985<br>899<br>1010/799 |
| SnF + 1% ZnP, 0.75% SnPyro, 1.2% Buffer (Composition D) | 4 wks<br>(25 C./40 C.)<br>8 wks<br>13 wks | 0.65 | 0.44/0.40 | 0.25 | 0.26/0.20 | | 1052/981 |
| SnF + 1% ZnP, 1% SnPyro, 1.2% Buffer (Composition E) | 4 wks<br>(25 C./40 C.)<br>8 wks<br>13 wks | 0.59 | 0.56/0.53<br>0.58/0.55<br>0.58/0.54 | 0.23 | 0.26/0.29<br>0.25/0.27<br>0.29/0.28 | 1112 | 1042/981<br>1024/909<br>979/874 |

Example 3

Table 3 demonstrates the buffer composition used in above Examples 1-3.

TABLE 3

| Test Comp. | Buffer System (wt %) | |
|---|---|---|
| | Sodium Citrate* | Citric Acid |
| Test Compositions w/o Buffer | 0.00 | 0.00 |
| Compositions with 1.2% Buffer | 1.0 | 0.2 |

The water concentration of the above formulations is between 17.0% to 21.0% by wt. These are considered "high water" formulations. Therefore, the Applicants have addressed the instability of stannous ions without having to resort to either a) low water formulations; or b) dual phase compositions.

Example 4

TABLE 4

Stannous Uptake in Aerobic Biofilm (units in (ppm))

| | 1st Trt. | 2nd Trt. | 3rd Trt. | 4th Trt | 5th Trt | 6th Trt |
|---|---|---|---|---|---|---|
| SnF + 1% ZnP, 0.2% SnPyro, 1.2% Buffer (Comp. 1) | 3.19 | | 8.71 | | | 11.6 |
| SnF + 1% ZnP, 0.3% SnPyro, 1.2% Buffer (Comp. 2) | 3.69 (3.88) | 5.27 | 7.98 (10.44) | 1.2 | 10.59 | 12.52 (12.91) |
| SnF + 1% ZnP, 0.5% SnPyro, 1.2% Buffer (Comp. 3) | 6.21 | | 13.69 | | | 16.82 |
| SnF + 1% ZnP, 0.75% SnPyro, 1.2% Buffer (Comp. 4) | 6.18 | 8.91 | 14.98 | 21.74 | 17.31 | 20.98 |
| SnF + 1% ZnP, 1.0% SnPyro, 1.2% Buffer, (Comp. 5) | 7.27 (6.81) | 10.84 | 13.87 (15.59) | 17.71 | 23.58 | 23.07 (25.99) |

TABLE 4-continued

Stannous Uptake in Aerobic Biofilm
(units in (ppm))

|  | 1st Trt. | 2nd Trt. | 3rd Trt. | 4th Trt | 5th Trt | 6th Trt |
|---|---|---|---|---|---|---|
| SnF + 1% ZnP, 1.0% SnPyro, 1.2% Buffer, 12.3% Water (Comp. 6) | 6.9 | 9.92 | 16.48 | 18.02 | 18.91 | 20.98 |
| 0.454% SnF, Zn Lactate (Positive Control) | 1.61 (1.11) | 2.17 | 3.41 (2.69) | 3.42 | 6.34 | 4.56 (7.05) |

\* Numbers included in parenthesis indicate a second experimental run was conducted.
\*\* The designation "Trt" is understood to refer to "Treatment".
\*\*\* "Buffer" refers to an 1.2% by wt. organic acid buffer comprising 1.0% by wt Sodium Citrate, and 0.2% by wt. Citric Acid. The % wt. of the Sodium Citrate and Citric Acid refers to their amounts relative to entire composition.

The aerobic biofilm model quantifies the ability of the compound to prevent maturation of biofilm consisting of salivary inoculum on an artificial tooth surface (or hydroxyapatite (HAP)), through repeat treatment during a 5-day period. On Day 1, Hydroxyapatite discs on an Active Attachment Lid are incubated in clarified, sterilize-filtered saliva to form pellicle, treated, inoculated in whole human saliva suspended in media, and incubated before repeating treatment at end of day. The treatments are repeated every morning on Day 2-5.

After each treatment, each HAP discs containing biofilm are transferred to tubes containing 1 ml Aqua regia which is a mixture of nitric acid and hydrochloric acid used to dissolve metals or acid digest. The tubes are kept under a fume hood overnight to ensure full acid digestion. The samples are centrifuged to pellet the debris. The acid supernatant (aqueous portion) is transferred into another clean tube and brought up to volume to make a 10% acid solution using sterile water (1 ml supernatant: 9 ml water). This sample is sent to analytical for metal detection. The data is represented as parts per million (ppm) and as well as metal uptake over 6 treatments.

As can be seen in Table 4, compositions with SnF, zinc phosphate, demonstrate much increased stannous uptake in the aerobic biofilm assay as compared to market backbone formulations containing Zinc Lactate as the zinc source, and Stannous Fluoride as the source for stannous.

The invention claimed is:

1. An oral care composition comprising:
   a zinc source comprising zinc phosphate;
   a first source of stannous, wherein the stannous comprises stannous fluoride; and
   a second source of stannous, wherein the second source of stannous comprises stannous pyrophosphate; and
   a citrate buffer system, wherein the buffer system comprises tri-sodium citrate and citric acid; and
   wherein the water concentration of the oral care composition is between 15.0% to 35.0% by wt. of the composition.

2. The oral care composition of claim 1, wherein the zinc phosphate is a preformed salt of zinc phosphate.

3. The oral care composition of claim 1, wherein the zinc phosphate is present in an amount sufficient so that the stannous fluoride dissociates to provide a therapeutically effective amount of stannous ions in aqueous solution.

4. The oral care composition of claim 1, wherein the amount of zinc phosphate is from 0.05 to 10% by weight, relative to the weight of the oral care composition.

5. The composition of claim 1, wherein the first stannous ion source further comprises a stannous source selected from stannous chloride dihydrate, stannous pyrophosphate, stannous formate, acetate, gluconate, lactate, tartrate, oxalate, malonate citrate, stannous ethylene glyoxide, and a mixture thereof.

6. The composition of claim 1, wherein the first stannous ion source is stannous fluoride.

7. The composition of claim 1, wherein the composition comprises an effective amount of one or more alkali phosphate salts selected from sodium phosphate dibasic, potassium phosphate dibasic, dicalcium phosphate dihydrate, calcium pyrophosphate, tetrasodium pyrophosphate, tetrapotassium pyrophosphate, sodium tripolyphosphate, disodium hydrogen orthophosphate, monosodium phosphate, pentapotassium triphosphate and mixtures of any of two or more of these by weight of the composition.

8. The composition of claim 1, wherein the alkali phosphate salt is tetrapotassium pyrophosphate.

9. The composition of claim 1, wherein the alkali phosphate salt is sodium tripolyphosphate.

10. The composition of claim 1, wherein the composition comprises:
    a. Zinc phosphate about 1.0 wt %
    b. Stannous pyrophosphate about 0.2 wt %
    c. Tetrasodium pyrophosphate about 2.0 wt %.

11. The composition of claim 1, wherein the composition comprises:
    a. Zinc phosphate about 1.0 wt %
    b. Stannous pyrophosphate about 0.3 wt %
    c. Tetrasodium pyrophosphate about 2.0 wt %.

12. The composition of claim 1, wherein the composition comprises:
    a. Zinc phosphate about 1.7 wt %
    b. Stannous pyrophosphate about 1.0 wt %
    c. Tetrasodium pyrophosphate about 2.0 wt %.

13. A method to improve oral health comprising applying an effective amount of the oral composition of claim 1, wherein the oral care composition is applied to the oral cavity of a subject in need thereof.

\* \* \* \* \*